United States Patent [19]

Edrich

[11] 4,275,741
[45] Jun. 30, 1981

[54] PROCEDURE FOR NONCONTACTING MEASUREMENT OF SUBCUTANEOUS TEMPERATURE DISTRIBUTIONS

[76] Inventor: Jochen Edrich, Waldpromenade 83, Gauting, Fed. Rep. of Germany, 8035

[21] Appl. No.: 66,076

[22] Filed: Aug. 13, 1979

[51] Int. Cl.³ .............................................. A61B 6/00
[52] U.S. Cl. .................................. 128/653; 128/736; 73/355 R
[58] Field of Search ...................... 128/653, 664, 736; 73/355 R; 250/316.1

[56] References Cited

U.S. PATENT DOCUMENTS

| 3,335,716 | 8/1967 | Alt et al. | 128/736 |
| 3,970,074 | 7/1976 | Mogos et al. | 128/736 |

OTHER PUBLICATIONS

Culliton, B. J., *Science*, vol. 193, (1976), p. 555.
Barrett, A. H. et al., *Radio Science*, vol. 12, (1977), pp. 167–171.
Edrich, J. et al., *Journ. of Rheumatology*, vol. 5, (1978), No. 1, pp. 59–67.

Gautherie, M. et al., *Functional Explorations in Senology*, Ghent/Belgium, Europ. Press, p. 93, 1976.
Moskowitz, M. et al., *New England J. of Med.*, vol. 295, No. 5, (1976), pp. 249–252.

*Primary Examiner*—Kyle L. Howell
*Attorney, Agent, or Firm*—Robert C. Dorr

[57] ABSTRACT

A method for noncontacting measurement and imaging of subcutaneous temperature distributions for the early detection of tumors. The (black-body) thermal electromagnetic radiation emitted by hyperthermic tumorous tissues is collected, focussed and detected within several frequency bands from 8 GHz to 36 GHz using a specially designed light-weight elliptical reflector and a highly sensitive broadband radiometer which are scanned in a raster type fashion over the supine patient. Direct indication of subcutaneous temperatures, microcomputer-aided data processing, and color or grey scale image display provide clinically usable subcutaneous thermograms at several depths which, together with conventional cutaneous infrared thermograms, can be utilized for the early detection and mass screening of tumors such as breast cancer.

3 Claims, 1 Drawing Figure

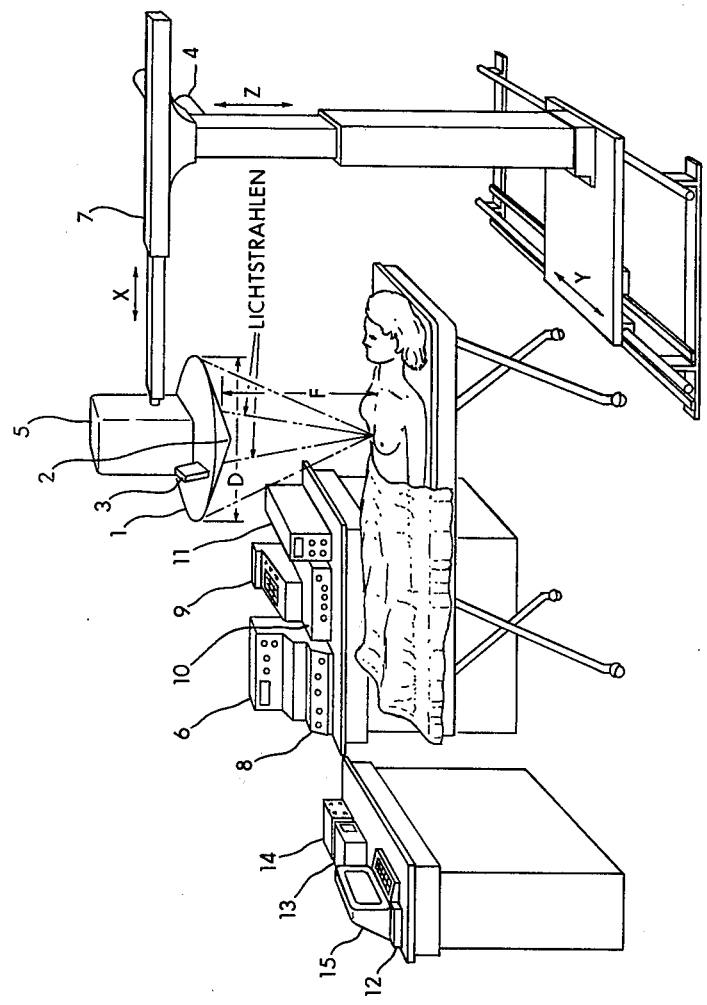

PROCEDURE FOR NONCONTACTING MEASUREMENT OF SUBCUTANEOUS TEMPERATURE DISTRIBUTIONS

BACKGROUND OF THE INVENTION

1. Field of the Invention

This invention relates to thermographic measurements for the detection and measurement of thermal abnormalities of the human body, and more particularly to noncontacting measurement of subcutaneous temperature distributions for early detection of tumors.

2. Discussion of the Prior Art

X-ray techniques for the detection or measurement of structural abnormalities or diseases of the human body are being used more frequently (mammography, CT scanning, etc.). The disadvantage of these diagonstic methods is radiation exposure to the patient (B.J. Culliton, Science, vol. 193, (1976), p. 555); they are also clinically ineffective for common inflammatory processes where only temperature changes occur. Like, for example, in the most common form of arthritis (J. Edrich and C. J. Smyth, "Arthritis Inflammation Monitored by Subcutaneous Millimeter Wave Thermography", Journal of Rheumatology, vol. 5, (1978), No. 1, p. 59–67) and in the early stages of certain tumors (M. Gautherie, Y. Quenneville and Ch. Gros, in "Functional Explorations in Senology", Europ. Press, Ghent/Belgium; p. 93, 1976). For the above applications, both infrared and plate thermography are used. These methods lead to images with good temperature and spatial resolution. Both, however, are not suited for precise measurements of subcutaneous temperature distributions because the temperature of the skin—as opposed to the subcutaneous temperature—can change significantly, i.e., several degrees and the correlation with subcutaneous processes—tumors, inflammations, etc.—is thus small. These methods therefore cannot in general be considered suitable for the early detection of breast and brain tumors (M. Moscowitz, J. Milbrath, P. Cartside, A. Zermano and D. Mandel, "Lack of Efficacy of Thermography as a Screening Tool for Minimal and Stage I Breast Cancer", New England Journal of Med., vol. 295, (1976), No. 5, p. 249–252).

Good penetration depths of several centimeters have been achieved with contacting thermography at a wavelength of about 10 cm (A. H. Barrett, P. C. Myers and N. L. Sadowsky, "Detection of Breast Cancer by Microwave Radiometry", Radio Science, vol. 12, (1977), p. 167–171). This method, however, is used in a stethoscopic fashion, and is therefore impractical; the results are also not readily reproducible because of the critical influence of miniscule air gaps. In addition, it can not localize a subcutaneous process and is restricted to integrating measurements of relatively large volumes of subcutaneous temperature distributions without precise depth determination.

Experiments to avoid these disadvantages using contactless subcutaneous temperature measurements of the human body have been reported (J. Edrich and C. J. Smyth, "Arthritis Inflammation Monitored by Subcutaneous Millimeter Wave Thermography", Journal of Rheumatology, vol. 5, (1978), No. 1, p. 59–67). Here, subcutaneously emitted thermal (black-body) electromagnetic radiation at a wavelength of 4 mm (68 GHz) was detected using a focussed arrangement which yielded a spatial resolution of slightly more than ⅓ wavelength. The power was radiometrically detected within a bandwidth of 2 GHz, integrated with a time constant of 1 to 3 seconds, and recorded. Other experiments were performed in the frequency range 66 to 71 GHz with a bandwidth of 2 GHz. The method has been used for the detection of arthritis in knee joints and breast cancer. Shorter integration times can be used for larger received powers. It is desirable to use the shortest integration time possible, with a permissible temperature fluctuation, in order to achieve short imaging times.

For the purpose of focussing the subcutaneously emitted radiation into the horn of the receiving system (radiometer), lenses made of dielectric material (plastic) were used which had a diameter of 20 to 25 cm and a thickness of about 5 cm. For adjustment of the focal distance, two light sources with point or "V" images were attached on each side of the lense; the space between their images on the skin indicated the depth of the subcutaneous focus. Crossing of these focussed light beams indicated the focal spot.

Satisfactory detection of deeper lying tumors, inflamed regions, or temperature abnormalities was not possible for depths of 2 to 4 cm or more although the emissivity of skin, and achievable spatial resolution, were attractive and allowed the use of conveniently sized lenses above 60 GHz. Hence, attempts were made to achieve higher detection sensitivities using larger lenses. It was soon discovered, however, that one was reaching both manufacturing as well as clinical limits as the lenses had to be made extraordinarily large. This also increased the disturbing influence of reflections and absorption.

DESCRIPTION OF THE DRAWING

FIG. 1 illustrates the system utilizing the method of the present invention.

The invention is described by the example given in FIG. 1 drawing which shows an apparatus realizing the invention. It also shows the supine patient on a tilted bed.

This instrument is used for early detection of breast cancer. The thermal radiation emitted in the microwave frequency range of 8 to 36 GHz by a subcutaneous mamma carcinoma is focussed by use of an elliptical reflector 1 into the receiving horn 2 of the receiving system 5 (highly sensitive radiometer) which is connected with the horn through a bent waveguide or coaxial line. The elliptical reflector has a short object focal length f (f/D=0.6 to 1.2, where D is the diameter of the aperture or reflector).

Two focussing light sources 3 with point or "V"-type images "cross" visible light beams at the subcutaneous object focal spot thus indicating the depth of temperature measurement by their spacing on the skin. This facilitates the adjustment of the reflector height above the desired subcutaneous object focus. Their reflected image is utilized to automatically control the scanner height adjustment in Z direction with the help of infrared or photo-detectors which are attached to the receiving horn in a noninterfering fashion, and the focussing or height adjusting motor 4. Scanning is performed in raster fashion along a line (Y-direction) and orthogonal to that line (X-direction) by automatic movements of the arm 7 supporting the reflector 1 and the radiometer 5. Scanning speed, line length and line spacing are preset at the controller 8. The output of the instrument 6 indicating the temperature in degrees centigrade is connected with a strip chart or XY recorder. The temperature and scanning signals—the latter ones containing the XY information—are also frequency modulated and stored at the lowest speed of the tape recorder 10. At the completion of the measurement the tape is played back at highest speed and the demodulated signals are fed into the oscillographic grey scale display 11. Hard copies of the grey scale image are obtained by a photographic camera.

Subsequent image processing is performed in the microcomputer 12 together with the minidisc 13. The thermographic image (temperature and XY signals) is first digitized and stored in matrix format. In the next step, various averages are computed which are needed for correlating the thermographic images of the left and right breasts. Subsequently, isothermes are constructed and the prefiltering and smoothing operations are performed as subsequently described. Finally, the image is converted in the grey scale converter 14 and displayed on the video display in color or grey scale, significantly improved and smoothened. It may now be photographed with or without the mentioned space-averaged temperature date and read by a physician.

It is to be expressly understood that the various components recited above are conventional and are readily available commercially.

It was the purpose of this invention to present a method for contactless subcutaneous temperature measurement giving a higher temperature sensitivity together with good spatial resolution which allows detection of deeper lying temperature changes of a small order. This measurement is necessary for reliable early detection of tumors and arthritis. The method also permits shorter imaging times so as to reduce or even completely eliminate the influence of slight temperature changes and body movements during the measurements.

The solution of this task was achieved by choosing to monitor thermal electromagnetic radiation emission in the 8 to 36 GHz frequency range using an elliptic focussing reflector; the aperture of this reflector was chosen to lie between 50 and 100 centimeters and the object distance was made between 0.6 and 1.2 times the aperture width.

The receiving horn is placed at the image focal spot of the elliptic reflector, whereas the object focal spot of the reflector is "placed" into the subcutaneous region to be measured. Particularly high resolution is achievable with an image distance that is 0.8 to 1 times the aperture dimension.

The selected frequency range used in prior experiments was generally regarded as unsuitable because of the combination of strong reflections and impractically large dielectric lenses. However, under the teachings of the present invention, specifically, the special elliptic near-field focussing arrangement, the limitations of previous methods are overcome while still retaining good subcutaneous resolution.

Another advantage of the new procedure as compared to well-known ones is its 3 to 4 times higher speed. It also yields a higher detection rate, particularly for depths of 1 to several centimeters depending on the type of tissue. Furthermore, it results in excellent temperature resolution and has excellent disease localizing capabilities in all three dimensions.

Additionally, an even more sensitive and faster localization of subcutaneous temperature abnormalities is possible in the given frequency range by multispectral detection and measurement. Here, several frequency bands (each 2–5 GHz wide) are simultaneously received and processed. This way each scanning measures at several different depths (for example three depths) and therefore allows an immediate determination of the depth distribution of subcutaneous temperature, producing 3-D like (tomographic) temperature images. The processing of the different frequency bands is simultaneous, although initially separate.

During scanning along a straight line, the distance of the reflector from the body surface changes resulting in a measurement of temperatures at different depths. It is now possible to use automatic focussing by utilizing two focussed light sources with point or "V" images. The light sources are attached to each side of the reflector apex and are used to control the distance in a well known way. In order to keep focussing deviations to a minimum, the reflector scan lines of the receiving system are arranged in such a way that distance variations in the scanned region are minimized.

It is also noted that optimum measurement of breast temperatures is obtained if the suprine patient is turned about the long body axis by about 30°. In this way the breast is more evenly supported by the chest. This artifically oblique supine position results in particularly well focussed images, a reduction of the strongly frequency-dependent variations of emissivity (caused by changing incidence angles), and an optimum right-left symmetry for thermographic comparisons of the right and left breast.

From the completed thermographic image (thermogram). temperature averages can be determined after digitization and interim storage of the data in matrix format. These averages can then be correlated with averages of the contralateral breast. In this way, differences or abnormalities of the left-right symmetry of subcutaneous temperature distributions can be used to establish tumor probability since the subcutaneous temperature distribution of healthy breasts exhibits good left-right symmetry.

One can also construct isothermes from these temperature data, which can then be prefiltered and "smoothened" in a well known way and be displayed. Such processing facilities the reading of thermograms since the wavelength-limited emission resolution produces coarser isothermes than are physically possible.

The invented procedure is practically realized by an apparatus with a radiometric receiving system for the measurement of scanned subcutaneously emitted thermal electromagnetic radiation in the microwave region. The receiving system is specifically designed for the reception of thermal radiation in the frequency range from 8 to 36 GHz. The focussing apparatus is an elliptical receiving reflector with an aperture between 50 cm and 100 cm, and an object focal length which is 0.6 to 1.2 times the aperture diameter. The receiving horn is located in the image focal spot of the focussing apparatus. For near-field focussing the precision of the focussing apparatus is very important. Therefore the receiving reflector is spun from suitable aluminum sheets of a thickness of 1 to 2 mm. This method has the advantages of extreme light weight, high precision and stability of form, and low cost. Reflectors with more weight, such as those produced by casting or turning on a lathe are avoided. Alternative solutions could utilize relatively thick reflectors made out of plastic or foam with homogenious metal coatings on the inside.

Although the present invention has been described with a certain degree of particularity, it is understood that the present disclosure has been made by way of example and that changes in details may be made without departing from the spirit thereof.

I claim:

1. An improved method for noncontacting measurement of subcutaneous body temperature distributions, said method detecting the emitted thermal electromagnetic radiation in the microwave region from subcutaneous points having a diameter of substantially one-third wavelength focussed along predetermined scan lines, said improved method comprising the steps of:

detecting said radiation in the frequency range of 8 to 36 GHz, focussing said detected radiation with an elliptical receiving reflector having an aperture diameter of between 50 to 100 cm and having a focal length of 0.6 to 1.2 times the aperture diameter.

2. The method of claim 1 further including the step of simultaneously detecting multi-spectral radiation in different frequency bands in said frequency range.

3. An improved method for noncontacting measurement of subcutaneous body temperature distributions in the breast of a person, said method detecting the emitted thermal electromagnetic radiation in the microwave region from subcutaneous points in said breast focussed along predetermined scan lines, said improved method comprising the step of rotating the breast by an angle of about 30 degrees about the long body axis of said person away from the normal, supine position so that said breast is evenly supported by the chest of said person.

* * * * *